US006555375B1

(12) United States Patent
Golovko

(10) Patent No.: US 6,555,375 B1
(45) Date of Patent: Apr. 29, 2003

(54) METHODS FOR SOMATIC EMBRYO FORMATION AND PLANT REGENERATION OF BETA VULGARIS

(75) Inventor: Andrei E. Golovko, West Ampton, NJ (US)

(73) Assignee: American Cyanamid Company, Parsippany, NJ (US)

( * ) Notice: Subject to any disclaimer, the term of this patent is extended or adjusted under 35 U.S.C. 154(b) by 308 days.

(21) Appl. No.: 09/593,342

(22) Filed: Jun. 14, 2000

(51) Int. Cl.[7] ............................... C12N 5/00; C12N 5/02

(52) U.S. Cl. ...................... 435/430.1; 435/420; 435/430

(58) Field of Search .............................. 435/420, 430.1, 435/430

(56) References Cited

U.S. PATENT DOCUMENTS 5,821,126 A 10/1998 Durzan et al.

FOREIGN PATENT DOCUMENTS

WO    WO 91/13159 A2    9/1991

OTHER PUBLICATIONS

Somatic Embryo genesis from zygotic embryos of sugar beet *Beta vulgaris*. Paul Tenning et al. Plant science, 81(1992) 103–109.*
Buchheim, J., et al., "Maturation of Soybean Somatic Embryos and the Transition to Plantlet Growth," *Plant Physiol.*, 1989, pp. 768–775, vol. 89.
Finer, J.J., and A. Nagasawa, "Development of an Embryogenic Suspension Culture of Soybean (*Glycine max*Merrill.)," *Plant Cell, Tissue and Organ Culture*, 1988, pp. 125–136, vol. 15, Kluwer Academic Publishers, Dordrecht, Netherlands.
Finer, J., "Apical Proliferation of Embryogenic Tissue of Soybean [*Glycine max* (L.) Merrill]*, " *Plant Cell Reports*, 1988, pp. 238–241, vol. 7, Springer–Verlag.
Gray, D. et al., "Somatic Embryogenesis and Development of Synthetic Seed Technology," *Critical Reviews in Plant Sciences*, 1991, pp. 33–61, vol. 10(1), CRC Press, Inc.
Jacq, B., et al., "Efficient Production of Uniform Plants from Cotyledon Explants of Sugarbeet (*Beta vulgaris* L.)," *Plant Breeding*, 1993, pp. 185–191, vol. 110, 1993 Paul Parey Scientific Publishers, Berlin and Hamburg.
Kaneda, Y., et al., "Combination of Thidiazuron and Basal Media with Low Salt Concentrations Increases the Frequency of Shoot Organogenesis in Soybeans [*Glycine max* (L.) Merr.]," *Plant Cell Reports*, 1997, pp. 8–12, vol. 17, Springer–Verlag.
Krens, F.A., and D. Jamar, The Role of Explant Source and Culture Conditions on Callus Induction and Shoot Regeneration in Sugarbeet (*Beta vulgaris* L.), *J. Plant Physiol.*, 1989, pp. 651–655, vol. 134, Gustav Fischer Verlag, Stuttgart.

Kulshreshtha, S., and R.H.A. Coutts, "Direct Somatic Embryogenesis and Plant Regeneration from Mature Sugarbeet (*Beta vulgaris* L.) Zygotic Cotyledons," *Plant Growth Regulation*, 1997, pp. 87–92, vol. 22, Kluwer Academic Publishers, Netherlands.
Lai, F.M., and B. McKersie, "Scale–up of Somatic Embryogenesis in Alfalfa (*Medicago sativa* L.) I Subculture and Indirect Secondary Somatic Embryogenisis," *Plant Cell, Tissue and Organ Culture*, 1994, pp. 151–158, vol. 37, Kluwer Academic Publishers, Netherlands.
Lenzner, S., et al., "Plant Regeneration from Protoplasts of Sugar Beet (*Beta vulgaris*)," *Physiologia Plantarum*, 1995, pp. 342–350, vol. 94, Denmark.
Liu, W., et al., "Somatic Embryo Cycling: Evaluation of a Novel Transformation and Assay System for Seed–Specific Gene Expression in Soybean," *Plant Cell, Tissue and Organ Culture*, 1996, pp. 33–42, vol. 47, Kluwer Academic Publishers, Netherlands.
Longbiao, M., and G. Jiufeng, "A Study on Genotype Screening of Sugarbeet and the Establishment of Embryonic Cell Lineage," *China Sugarbeet*, 1994, pp. 8–11, vol. 3.
McGranahan, G.H., et al., "Improved Efficiency of the Walnut Somatic Embryo Gene Transfer System," *Plant Cell Reports*, 1990, pp. 512–516, vol. 8, Springer–Verlag.
Nielsen, J.M., et al., "Synergism of Thidiazuron and Benzyladenine in Axillary Shoot Formation Depends on Sequence of Application in *Miscanthus X ogiformis* 'Giganteus'," *Plant Cell, Tissue and Organ Culture*, 1995, pp. 165–170, vol. 41, Kluwer Academic Publishers, Netherlands.
Owens, L.D., and D. Eberts, "Sugarbeet Leaf Disc Culture: An Improved Procedure for Inducing Morphogenesis," *Plant Cell, Tissue and Organ Culture*, 1992, pp. 195–201, vol. 31, Kluwer Academic Publishers, Netherlands.
Roussy, I., et al., "*In Planta* 2,3,5 Triiodobenzoic Acid Treatment Promotes High Frequency and Routine In Vitro Regeneration of Sugarbeet (*Beta vulgaris* L.) Plants," *Plant Cell Reports*, 1996, pp. 142–146, vol. 16, Springer–Verlag.
Sato, S., et al., "Stable Transformation Via Particle Bombardment in Two Different Soybean Regeneration Systems," *Plant Cell Reports*, 1993, pp. 408–413, vol. 12, Springer–Verlag.
Tenning, P., et al., Somatic Embryogenesis from Zygotic Embryos of Sugar Beet (*Beta vulgaris* L.), *Plant Science*, 1992, pp. 103–109, vol. 81, Elsevier Scientific Publishers Ireland Ltd., Ireland.

(List continued on next page.)

Primary Examiner—Bruce R. Campell
Assistant Examiner—Annette H Para
(74) *Attorney, Agent, or Firm*—Alston & Bird LLP

(57) ABSTRACT

The present invention relates to plant tissue culture methods, particularly for *Beta vulgaris*. Methods are provided for producing callus tissues, somatic embryos and plants. The methods find use in the field of agricultural biotechnology, particularly in the production of transgenic *Beta vulgaris* plants.

30 Claims, 3 Drawing Sheets

OTHER PUBLICATIONS

Tétu, I., et al., "Hormonal Control of Organogenesis and Somatic Embryogenesis in *Beta vulgaris* Callus," *Journal of Experimental Botany*, Mar. 1987, pp. 506–517, vol. 38(188), Oxford University Press.

Wright, M., et al., "A Simple Method for the Recovery of Multiple Fertile Plants from Individual Somatic Embryos of Soybean [*Glycine max* (L) Merrill]," *In Vitro Cell. Dev. Biol.*, Jul. 1991, pp. 153–157, vol. 27P, 1991 Tissue Culture Association.

D'Halluin, K., et al., "Transformation of Sugarbeet (*Beta vulgaris* L.) and Evaluation of Herbicide Resistance in Transgenic Plants," *Bio/Technology*, Mar. 1992, pp. 309–314, vol. 10, Nature Publishing, USA.

Moghaddam, B., et al., "The Effect of In Planta TIBA and Proline Treatment on Somatic Embryogenesis of Sugar Beet (*Beta vulgaris* L.)," *Euphytica*, Jan. 2000, pp. 151–156, vol. 112(2).

Murthy, B., et al., "Thidiazuron: A Potent Regulator of In Vitro Plant Morphogenesis," *In Vitro Cellular & Development Biology–Plant*, Oct. 1998, pp. 267–275, vol. 34(4).

Zhang, C., et al., "Thidiazuron–Induced Organogenesis and Somatic Embryogenesis in Sugar Beet (*Beta vulgaris L.*)," *In Vitro Cellular & Development Biology–Plant*, Mar. 2001, pp. 305–310, vol. 37(2).

Biosis Database Report for Accession No. PREV199800218178, Mar. 1998 (XP–002197319).

Biosis Database Report for Accession No. PREV199900205118, Mar. 1998 (XP–002197320).

Biosis Database Report for Accession No. PREV199799370520, 1996 (XP–002197321).

Biosis Database Report for Accession No. PREV199698797564, 1996 (XP–002197322).

Biosis Database Report for Accession No. PREV199294089358, 1992 (XP–002197323).

* cited by examiner

Initial explant: sugarbeet hypocotile

Friable callus initiation

Proliferation of friable callus

Formation of embryos

Formation of repetitive embryos

Embryogenic tissues in liquid culture, dark

Conversion of embryo into mature plant

Sugarbeet plant of embryo origin 0.03 mg/l of TDZ was the best concentration to induce plant regeneration from a series of 0.03 – 3 mg/l.

METHODS FOR SOMATIC EMBRYO FORMATION AND PLANT REGENERATION OF *BETA VULGARIS*

FIELD OF THE INVENTION

The present invention relates to the field of agricultural biotechnology. The invention further relates to in vitro embryogenesis from somatic cells.

BACKGROUND OF THE INVENTION

About one-third of the world's sugar is refined from sugar beets. Unlike sugarcane which must be grown in tropical and subtropical regions of the world, sugar beets thrive in the temperate regions of the world. The sugar beet is the same taxonomic species (*Beta vulgaris* L.) as the common garden beet or red beet. Through the efforts of plant breeders, the sugar beet was bred from the garden beet by selection for increased sugar content in the root. The sugar beet breeders were able to increase the sugar content of the beet roots considerably. Compared to garden beets which have roots with a sugar content of in the range of 1–4%, the sugar content of the roots of modern sugar beet cultivars is in the range of 15–20%.

Despite the prominent position of the sugar beet in world sugar production, the rate of the development of new cultivars has been limited by a lack of efficient methods for producing transgenic sugar beets. The efforts of agricultural scientists to introduce important transgenic traits such as herbicide resistance and the resistance to diseases caused by pathogenic fungi and nematodes has been slowed by this lack of efficient methods for producing transformed sugar beet plants. While producing transformed sugar beet cells and tissues is not particularly difficult with methods such as biolistic transformation and Agrobacterium-mediated transformation, the production of transgenic sugar beet plants is limited by the lack of efficient protocols for regenerating the transformed cells and tissues into transformed sugar beet plants. Agricultural scientists need improved methods for producing transgenic sugar beet plants to provide sugar beet producers with new cultivars having the desired transgenic traits.

For some important crop species where regenerating transformed plants has proven difficult, agricultural scientists have developed methods which involve DNA delivery into isolated embryos because such embryos can be routinely regenerated into plants. Typically, either immature zygotic embryos or somatic embryos are used in such methods. A disadvantage of the use of immature zygotic embryos is that such embryos must be isolated from maternal plants at a specific developmental stage. Thus, to have a steady supply of embryos for transformation, one needs to maintain large numbers of plants of various ages. Somatic embryos can also be transformed and regenerated into transgenic plants, and are preferable over immature zygotic embryos, if relatively large numbers of somatic embryos can be produced routinely and efficiently. For important crops like soybean, repetitive embryogenic culture systems have been developed for the efficient production of somatic embryos for use in transformation (Sato et al. (1993) *Plant Cell Reports* 12:408–413).

SUMMARY OF THE INVENTION

Methods are provided for producing somatic embryos of *Beta vulgaris*. The methods find use in the agricultural biotechnology industry, particularly in methods for producing transgenic *Beta vulgaris* plants. The methods of the invention involve producing secondary somatic embryos comprising exposing a somatic embryo to initiation medium to induce the formation of an embryogenic tissue mass. The methods further involve isolating the embryogenic tissue mass and exposing the embryogenic tissue mass to proliferation medium to form embryogenic outgrowths. The methods further involve exposing the embryogenic outgrowths to regeneration medium to form secondary somatic embryos. The methods of the invention may additionally comprise a multiplying step to increase the number of secondary embryos produced. Such a multiplying step involves subdividing the expanded embryogenic tissue masses and exposing the subdivided tissues masses to fresh medium, particularly fresh proliferation medium. The multiplying step can be repeated one or more additional times to further increase the number of embryogenic outgrowths that can be regenerated into secondary embryos.

Methods are provided for producing *Beta vulgaris* plants from secondary somatic embryos. The methods involve producing secondary somatic embryos and regenerating such embryos into plants. The methods may additionally involve exposing shoots or germinated, secondary somatic embryos to rooting medium.

Methods are provided for producing transformed *Beta vulgaris* plants from secondary somatic embryos. The methods involve transforming a cell of a secondary somatic embryos with a gene of interest and regenerating such an embryo, or at least one transformed cell thereof, into a transformed Beta vulgaris plant.

Also provided are methods for producing callus tissues and regenerating such callus tissues into plants. The methods involve exposing seedling tissues, particularly hypocotyls and cotyledons, to a callus induction comprising at least one cytokinin, particularly thidiazuron. The methods further involve regenerating shoots that appear on callus tissues into *Beta vulgaris* plants.

Transformed *Beta vulgaris* plants, plant tissues and plant cells, and seeds thereof are also provided.

DETAILED DESCRIPTION OF THE INVENTION

Figure 1A:
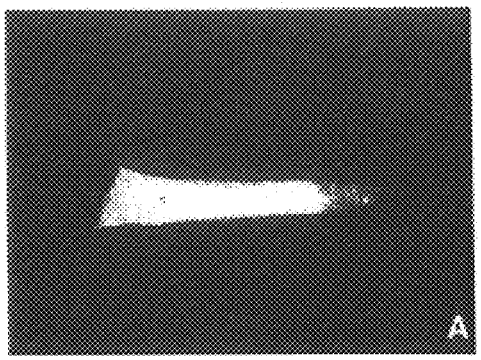
FIG. 1 is a photographic illustration of examples of selected stages of sugar beet tissues during somatic embryogenesis. (A) Initial explant: sugar beet hypocotyls. (B) Friable callus initiation. When explants become necrotic and dark brown, colonies of white friable callus appear on the explant surface. (C) Proliferation of friable callus. Several callus types as well as small regenerants are distinguished after the original callus was transferred to fresh medium. (D) Formation of embryos. White embryonic structure embedded in friable callus.

The invention is drawn to methods for producing callus tissues, somatic embryos and plants of *Beta vulgarism*. The methods find use in agriculture, particularly in the development of transgenic *Beta vulgaris* plants and in the production of artificial seeds.

A number of terms used herein are defined and clarified in the following section.

By "somatic embryo" is intended an embryo that develops from a somatic cell. The developmental process by which a somatic embryo develops from a cell is known as "somatic embryogenesis." Such a "somatic embryo" is distinct from a "zygotic embryo" which develops from a zygote.

By "secondary somatic embryo" is intended a somatic embryo that develops from tissues of a pre-existing somatic embryo. A somatic embryo that develops from the tissues of a secondary somatic embryo is also a secondary somatic embryo.

By "primary somatic embryo" is intended a somatic embryo that originates from tissues other than those of another somatic embryo.

By "primary shoot" is intended the shoot that develops from the root-shoot axis of an embryo.

By "adventitious" is intended to describe an organ or other structure of a plant that does not originate in its usual location on the plant body. For example, a shoot that originated from the tissues of a primary shoot or from callus tissue. is an "adventitious shoot."

By "effective amount" is intended an amount of an agent such as, for example, a phytohormone or other compound, that, when administered, is capable of causing the desired effect on a plant or part thereof including, but not limited to, whole plants, seeds, callus and isolated plant cells, tissues, organs and embryos in culture. It is recognized that an "effective amount" may vary depending on factors, such as, for example, the genotype of the plant, the target tissue, the method of administration, temperature, light, relative humidity and the like. Further, it is recognized that an "effective amount" of a particular agent can be determined by administering a range of amounts of the agent to the plant or part thereof and then determining which amount or amounts cause the desired effect.

By "auxin-free" is intended a plant culture medium which does not contain an auxin.

A first object of the present invention is to provide efficient methods for producing somatic embryos from *Beta vulgaris*. A second object of the invention is to provide methods for producing *Beta vulgaris* plants via somatic embryogenesis. A third object of the invention is provide methods for producing transformed *Beta vulgaris* plants. A fourth object of the invention is to provide methods for producing callus and regenerating such callus into plants. The methods of the invention find use in the production of genetically transformed *Beta vulgaris* plants, particularly genetically transformed sugar beet plants. The methods find further use in the propagation of sugar beet plants, particularly genotypes of sugar beet that cannot be reproduced routinely by methods involving sexual reproduction.

Methods are provided for producing secondary somatic embryos of *Beta vulgaris*. Such somatic embryos find use as a target tissue in methods for transforming *Beta vulgaris* plants, particularly sugar beet plants. Such somatic embryos also find use in producing synthetic seeds. The methods of the invention involve exposing a somatic embryo to initiation medium to induce the formation of an embryogenic tissue mass. The methods further involve isolating the embryogenic tissue mass and exposing the embryogenic tissue mass to proliferation medium.

The methods of the invention do not depend on a particular type of somatic embryo, only that such a somatic embryo is capable of producing at least one embryogenic tissue mass. Any somatic embryo can be used in the methods of the present invention including, but not limited to, somatic embryos developing from one or more cells of immature seeds, callus tissues and seedling tissues. Preferably, the somatic embryos are produced from callus tissues. More preferably, the somatic embryos are produced from friable callus tissues. Most preferably, the somatic embryos are produced from friable callus tissues that were produced by a method using seedling tissues.

Preferred methods of the invention involve somatic embryos that develop from friable callus tissue that was produced from seedling tissues. Such friable callus tissue can be produced comprising exposing seedling tissues to callus induction medium and then exposing friable callus produced therefrom to embryogenesis medium to induce the formation of somatic embryos.

Seedling tissues of the invention include, but are not limited to cotyledons, hypocotyls, radicles, epicotyls, meristems, petioles, leaves, roots, and axillary buds. Preferred seedling tissues are hypocotyls and cotyledons. Typically, the seedling tissues are from seedlings that are less than about one month old, or about one month after germination was initiated. Preferably, the seedlings are about two weeks old.

The seedlings may be grown by any method known in the art. The methods of the invention do not depend on *Beta vulgaris* seedlings grown by any particular method, only that tissues from such seedlings can be used to produce friable callus as disclosed herein. Typically, seeds are sown on or in a substrate such as, for example, a plant culture medium, soil, or a potting medium. Preferably, the seedlings are grown under aseptic conditions. The seeds can be sterilized or otherwise treated to reduce microbial contamination and then exposed to germination medium.

Methods for sterilizing seeds are known in the art. Generally, such methods involve incubating the seeds with one or more sterilization solutions comprising one or more antimicrobial agents that are known to kill microbes, particularly bacteria and fungi. Antimicrobial agents include, but are not limited to, household laundry bleach, sodium hypochlorite, calcium hypochlorite, hydrogen peroxide, ethanol and mercuric chloride. The sterilization solutions may also include a surfactant or detergent such as, for example, Tween 20 and sodium lauryl sulfate. Following the incubation, the seeds are typically rinsed several times with sterile distilled water.

In an embodiment of the invention, *Beta vulgaris* seeds, are soaked in water overnight and then washed under water flow from a faucet to remove the seed cover. The seeds are then transferred to a laminar flow hood and incubated sequentially in aqueous solutions of 70% (v/v) ethanol for 1 minute, 0.1% (w/v) mercuric chloride for 10 minutes and 10% (v/v) household laundry bleach for 20 minutes. The seeds are then rinsed four times with sterile distilled water before placing on sterile filter paper in a laminar flow hood to dry. The dried seeds are then placed in petri plates on the surface of solid germination medium comprising MS basal salts (Murashige and Skoog (1962) *Physiol. Plant.* 15:473–497) and an effective amount of a cytokinin including, but not limited to, 6-benzylaminopurine (BAP) at 2 mg/L and thidiazuron (TDZ) at 1 mg/L. The plates with the seeds are then incubated in the dark at 21° C. for a period of about one to about four weeks, preferably about two weeks. The seedlings that develop from the seeds can be used as source of seedling tissues for producing friable callus.

Before exposing the seedling tissues to callus induction medium, the desired seedling tissues can be excised from the seedlings. Preferably, the desired seedling tissues of *Beta vulgaris* seedlings are separated from undesired tissues by excision. If desired following excision, the desired seedling tissues, may be farther subdivided by excising the tissue into two or more pieces. Additionally, the seedling tissues or pieces thereof may be wounded by, for example, crushing, slicing, cutting, incising, compressing, squeezing and puncturing.

The seedling tissues of the invention are exposed to callus induction medium. Callus forms on or in such seedling tissues during or following exposure to callus induction medium. Generally, such callus forms in a period of time that is less than about two months after the seedling tissues are first exposed to callus induction medium. Preferably, such callus forms in about three weeks after the seedling tissues are first exposed to callus induction medium.

The callus induction media of the invention are any media known in the art that are capable of inducing the formation of callus, particularly friable callus. Such friable callus is known in the art and may be characterized generally as a loosely formed callus that readily crumbles or falls apart. Generally, such callus induction media comprise a basal salt mixture, at least one phytohormone and a carbon source.

Typically, plant culture media of the invention will comprise a basal salt mixture. Such basal salt mixtures are known in the art and include, but are not limited to, Murashige & Skoog (MS), N6, NB, Gamborg's, Linsmaier & Skoog, Nitsch & Nitsch and the like. Generally, the pH of the plant culture media of the invention will fall within the range of about 4 to about 7, particularly between about 5.5 and about 6.5.

Plant culture media of the invention may additionally comprise a carbon source. Typically, the carbon source is a form of reduced carbon, particularly sucrose. The methods of the invention do not depend on a particular carbon source, only that the carbon source may be metabolized by *Beta vulgaris*. In addition to sucrose, carbon sources include, but are not limited to, glucose, fructose, maltose, galactose, raffinose, stachyose, mannitol and sorbitol.

The phytohormones of the invention include, but are not limited to, both free and conjugated forms of naturally occurring phytohormones or plant growth regulators. Additionally, the phytohormones of the invention encompass synthetic analogues, inhibitors of the synthesis, degradation, conjugation, transport, binding or action, precursors of such naturally occurring phytohormones and any other compounds that are known to have a phytohormone-like effect on the growth and development of plants. Phytohormones include, but are not limited to auxins, cytokinins, abscisic acid, gibberellins and ethylene, and conjugates, synthetic analogues, inhibitors and precursors thereof.

Naturally occurring cytokinins and synthetic analogues of cytokinins include, but are not limited to, kinetin, zeatin, zeatin riboside, zeatin riboside phosphate, dihydrozeatin, isopentyl adenine, 6-benzylaminopurine (BAP) and thidiazuron (TDZ).

Naturally occurring auxins and synthetic analogues of auxins include, but are not limited to, indoleacetic acid (IAA), 3-indolebutyric acid (IBA), α-napthaleneacetic acid (NAA), 2,4-dichlorophenoxyacetic acid (2,4-D), 4-(2,4-dichlorophenoxy) butyric acid, 2,4,5-trichlorophenoxyacetic acid (2,4,5-T), (4-chloro-2-methylphenoxy)acetic acid (MCPA), 4-(4-chloro-2-methylphenoxy) butanoic acid (MCPB), mecoprop, dicloprop, quinclorac, picloram, triclopyr, clopyralid, fluroxypyr and dicamba.

Inhibitors of auxins include, but are not limited, inhibitors of enzymes in the biosynthesis pathway leading to the formation of an auxin in a plant and auxin transport inhibitors, such as, for example, 3,4,5-triiodobenzoic acid (TIBA), naphthylphthalamic acid and 9-hydroxyfluorene-9-carboxylic acid. Inhibitors of ABA biosynthesis include, but are not limited to, norflurazon. Inhibitors of ethylene include, but are not limited to, inhibitors of ethylene synthesis or evolution such as, for example, aminoethoxyvinylglycine (AVG) and silver ions, and inhibitors of ethylene action such as, for example, 2,5-norbornadiene.

The plant culture media of the invention may additionally comprise other components known in the art such as, for example, vitamins, co-factors, micronutrients, charcoal, trace elements, myo-inositol, amino acids and the like. Solid plant culture media of the invention additionally comprise a solidifying agent such as, for example, agar. The plant culture media of the invention may also be adapted for use in transformation methods and may additionally comprise selective agents, such as, for example, antibiotics and herbicides. Such selective agents are known in the art and include, but are not limited to, kanamycin, geneticin, cefotaxime, carbenicillin, hygromycin, glyphosate, glufosinate or phosphinothricin, bialaphos, chlorsulfuron, bromoxynil, imidazolinones, 2,4-D and methotrexate.

Preferred callus induction media of the invention comprise an effective amount of at least one cytokinin. In certain embodiments of the invention, callus induction medium comprises the cytokinin TDZ. For the production of friable callus and shoots, and plants therefrom, a callus induction medium comprising TDZ is superior to a similar callus induction comprising the more commonly used cytokinin, BAP. For the production of somatic embryos, friable callus produced on a callus induction medium comprising BAP is preferred over a similar medium comprising TDZ. More preferred callus induction media comprise an effective amount of at least one cytokinin, a basal salt mixture, and sucrose. Most preferred callus induction media comprise an effective amount of BAP or TDZ, MS basal salts and sucrose.

The embryogenesis media of the invention include, but are not limited to, any medium known in the art that is capable of inducing the formation of somatic embryos from callus, particularly friable callus, when such somatic embryos are exposed to such a medium. The embryogenesis media of the invention comprise a basal salt mixture and a carbon source. Preferred embryogenesis media comprise a basal salt mixture, a carbon source and an effective amount of at least one phytohormone. Such an effective amount is an amount that is capable of inducing embryo formation in or on callus tissues when the callus tissues are exposed to a medium comprising such an effective amount of a phytohormone. More preferred embryogenesis media comprise a basal salt mixture, sucrose and an effective amount of at least one cytokinin. Most preferred embryogenesis media comprise MS basal salts, sucrose and an effective amount of BAP or TDZ.

After the callus tissues of the invention are first exposed to embryogenesis medium, somatic embryos generally form within about six weeks or less. Preferably, such somatic embryos form in about four weeks or less. More preferably, such somatic embryos form in about three weeks or less.

In an embodiment of the invention, callus induction medium comprises MS basal salts, 3% (w/v) sucrose, 100 mg/L myo-inositol, 0.5 mg/L nicotinic acid, 0.5 mg/L pyridoxine-HCl, 1 mg/L thiamine-HCl, 0.8% (w/v) Difco agar, and an effective amount of a cytokinin. Preferably, the cytokinin is BAP at 2 mg/L or TDZ at 1 mg/L. Explants from seedling tissues, preferably incised pieces of hypocotyl or cotyledon tissue are incubated in the dark at 21° C. for two to six weeks, preferably about four weeks. By "incised" is intended that the pieces are cut or sliced into with a sharp instrument such as, for example, a scalpel. Following such an incubation, the explants are generally necrotic and dark brown with white friable callus appearing on the explant surface. The friable callus can be separated or excised from the explant and transferred to embryogenesis medium comprising MS basal salts, 3% (w/v) sucrose, 100 mg/L myo-inositol, 0.5 mg/L nicotinic acid, 0.5 mg/L pyridoxine-HCl, 1 mg/L thiamine-HCl, 0.8% (w/v) Difco agar, and an effective amount of a cytokinin, such as, for example, BAP at 1 mg/L or TDZ at 1 mg/L. Generally, embryos begin to appear after about two weeks of incubation in the dark at 21° C. For further growth, the young somatic embryos can be transferred to fresh embryogenesis medium or a similar medium that lacks phytohormones.

The methods of the invention involve exposing a somatic embryo to initiation medium. The invention does not depend on a particular initiation medium, only that such a medium is capable of inducing the formation of embryogenic tissue masses on or in the tissues of an embryo. Any plant culture medium known in the art that is capable of inducing the formation of such embryogenic tissue masses may be employed in the methods of the invention.

Preferred initiation media of the invention comprise a basal salt mixture and an effective amount of at least one cytokinin. Such an effective amount of a cytokinin is an amount that is capable of inducing the development of embryogenic tissue masses on an embryo. More preferred initiation media comprise MS basal salts and an effective amount of at least one cytokinin. Most preferred initiation media comprise MS basal salts and 1 mg/L BAP. It is recognized that such preferred initiation media may additionally comprise: a carbon source such as, for example, sucrose; and vitamins and other co-factors, including, but not limited to, myo-inositol, nicotinic acid, pyridoxine-HCl, thiamine-HCl, and the like. If a solid initiation medium is desired, then an initiation medium of the invention may additionally comprise a solidifying agent such as agar.

The methods of the invention involve embryogenic tissue masses developing from the cells of somatic embryos. An embryogenic tissue mass of the invention can be a proembryo or other mass of cells which is capable of giving rise to embryogenic outgrowths when isolated and exposed to proliferation medium. Preferably, such outgrowths are white in color. An embryogenic tissue mass of the invention can form anywhere on a somatic embryo and can develop during the germination of the embryo. In preferred methods of the invention, the embryogenic tissue mass forms at or near the meristem region of a shoot apex during the germination of a somatic embryo on initiation medium. By "shoot apex" is intended the region at, or in the vicinity of the apical meristem, of a shoot. Typically, such an embryogenic tissue mass appears as a white inclusion embedded in, or in the vicinity of, the swollen meristem of a shoot of a germinating somatic embryo. Such a shoot can be the primary shoot or an adventitious shoot.

The embryogenic tissue masses of the invention can arise in shoot apices of embryos, particularly somatic embryos, at or in the vicinity of the meristem. The present invention does not depend on any particular method of producing such embryogenic tissue masses. In certain embodiments of the invention, such embryogenic tissue masses are white in color and arise in the shoot apices of somatic embryos during germination on media comprising at least one cytokinin, particularly BAP or TDZ.

Generally the embryogenic tissue masses appear within less than about six weeks after first exposing the somatic embryos to initiation medium, preferably in about four weeks or less, more preferably about three weeks or less, most preferably in about two weeks or less. Those of ordinary skill in the art will recognize, however, that the time necessary for such embryogenic tissue masses to appear can vary depending on a variety of factors, including, but not limited to the genotype of *Beta vulgaris,* the method by which the somatic embryos were produced, the age of the somatic embryos, the composition of initiation medium employed and environmental conditions during the production of the somatic embryos and during the exposure of the somatic embryos to initiation medium.

The methods of the invention additionally involve isolating the embryogenic tissue masses from the tissues of the somatic embryo. Preferably, the embryogenic tissue masses are isolated from the somatic embryos by excision. Once isolated, the embryogenic tissue masses are exposed to proliferation medium. Preferably, proliferation medium is a liquid medium. More preferably, proliferation medium is a liquid medium comprising a basal salt mixture, a carbon source and an effective amount of at least one cytokinin. Most preferably, proliferation medium is a liquid medium comprising MSE (MS basal salts, 100 mg/L myo-inositol, 0.5 mg/L nicotinic acid, 0.5 mg/L pyridoxine-HCl, 1 mg/L thiamine-HCl,), 0.1 mg/L BAP, 2 mg/L glycine, 6% (w/v) sucrose and a pH between about 4 and about 7.

Those of ordinary skill in the art will recognize that the concentration of components of such a proliferation medium can vary depending on a variety of factors known in the art including, but not limited to, the genotype of *Beta vulgaris* used and environmental conditions. Generally, an effective amount of a component of a proliferation medium is an amount that is optimal for the production of embryogenic outgrowths. While the methods of the invention do not depend on a particular cytokinin, the preferred cytokinin for proliferation media is BAP. Typically, the concentration of BAP in proliferation media is between about 0.01 mg/L and about 2 mg/L, preferably between about 0.05 mg/L and about 1 mg/L, more preferably between about 0.05 mg/L and about 0.1 mg/L. Proliferation medium may additionally comprise other phytohormones, particularly an auxin, more particularly a-naphthaleneacetic acid (NAA).

A proliferation medium of the invention will typically comprise a carbon source. The preferred carbon source is sucrose. Preferably, the concentration of sucrose in proliferation medium is a high concentration. By "high concentration" is intended a concentration that is greater than 3% (w/v). More preferably, the sucrose concentration is between 3% and about 8%. Most preferably, the sucrose concentration is about 6%.

A proliferation medium of the invention may additionally comprise any amino acid known in the art. Such amino acids include, but are not limited to glycine, glutamine and asparagine. The preferred amino acid of the invention for proliferation media is glycine or a combination of glycine and glutamine.

The methods of the invention involve exposing the embryogenic tissue masses to proliferation medium. In preferred methods of the invention, cultures are prepared by placing the embryogenic tissue masses in proliferation medium. The cultures are maintained in the dark at about 21° C. and subjected to rotation or shaking. Preferably, the cultures are rotated at a speed between about 25 rpm and about 250 rpm. More preferably, the cultures are rotated at a speed between about 50 rpm and about 150 rpm. Most preferably, the cultures are rotated at speed of about 100 rpm.

The embryogenic outgrowths develop from the embryogenic tissue masses that are exposed to proliferation medium. Within about one to about four weeks, preferably within about two weeks, exposure to proliferation medium, the embryogenic tissue masses expand and embryogenic outgrowths appear on the surface of the embryogenic tissue masses. The embryogenic outgrowths may then be excised from the embryogenic tissue masses and, if desired, exposed to regeneration medium for regeneration into secondary somatic embryos and if desired, later into plants.

The methods of the invention can additionally involve a multiplying step. Such a multiplying step can increase the number of secondary embryos produced. The multiplying step involves isolating embryogenic outgrowths, or part thereof, from the expanded embryogenic tissue masses and exposing such isolated embryogenic outgrowths to fresh medium, particularly fresh proliferation medium. The isolated embryogenic outgrowths, or part thereof, can be exposed to proliferation medium and maintained as described supra for embryogenic tissue masses for a period of time of about one to about four weeks, preferably about two weeks. At the end of such a period of time, the embryogenic outgrowths, particularly newly formed embryogenic outgrowths that develop from pre-existing embryogenic outgrowths, may be isolated and placed on regeneration medium for regeneration into secondary somatic embryos. Alternatively, the multiplying step can be repeated one or more additional times, before such regeneration, to further increase the number of embryogenic outgrowths.

Plant cultures comprising tissues that form embryos in a repetitive manner as disclosed herein above are sometimes referred to in the art as repetitive embryogenic cultures. Likewise, secondary somatic embryos that are formed on the plant tissues in such cultures are sometimes referred to as repetitive embryos.

The methods of the invention additionally involve regenerating embryogenic outgrowths into secondary somatic embryos. The methods comprise exposing embryogenic outgrowths to regeneration medium. The invention does not depend on a particular regeneration medium, only that such a medium is capable of inducing the development of a somatic embryo, particularly a secondary somatic embryo. Such regeneration media are known in the art. Preferred regeneration media of the invention are capable of inducing an embryogenic outgrowth to form at least one secondary somatic embryo. More preferred regeneration media are capable of inducing an embryogenic outgrowth to form at least one secondary somatic embryo, and inducing such an embryo to form a primary shoot. Most preferred regeneration media are capable of inducing an embryogenic outgrowth to form at least one secondary somatic embryo, and inducing such an embryo to form a primary shoot and at least one adventitious shoot.

Those of ordinary skill in the art of transforming plants will recognize that the formation of such adventitious shoots is desired in methods for transforming plants that involve embryos. The formation of such adventitious shoots can increase the number of transformed plants recovered per transformation attempt and also can increase the number of transformed plants recovered that are not chimeras of transformed and untransformed tissues.

In preferred methods of the invention, regeneration medium comprises an effective amount of a cytokinin. The preferred cytokinin for regeneration medium is TDZ. For regeneration, particularly shoot development on *Beta vulgaris* embryos, TDZ is superior to BAP. For inducing the formation of adventitious shoots on *Beta vulgaris* embryos, TDZ is also superior to BAP. Typically, the embryogenic outgrowths are exposed to regeneration medium for a period of less than about six weeks, preferably about three weeks. Preferably, regeneration medium comprises a basal salt mixture, a carbon source and an effective amount of a cytokinin. More preferably, regeneration medium comprises MS basal salts, sucrose and an effective amount of TDZ.

If necessary, an excised shoot or the entire germinated embryo may be transferred to rooting medium to induce or promote root development. Such rooting media are known in the art. While the invention does not depend on a particular rooting medium, preferred rooting media of the invention comprise an auxin, particularly indole butyric acid (IBA). Such rooting media include, but are not limited to, a medium comprising MS salts and 2 mg/mL IBA. Typically, the excised shoots or germinated embryos are exposed to rooting medium for less than about eight weeks, preferably about four weeks. After root formation, the plants may then be removed from culture, transferred to soil or other potting medium and subjected to any environmental conditions that are known in the art to favor growth, maturation and seed production.

The methods of the invention do not depend on particular culture conditions for regeneration or rooting. Any culture conditions known in the art to favor regeneration and/or rooting may be employed in the methods of the invention. Such culture conditions include, but are not limited to the light intensity, the photoperiod, and the temperature.

The methods of the invention can additionally involve transforming at least one cell of a secondary somatic embryo of the invention with a nucleotide construct comprising a gene of interest. The methods of the invention do not depend on a particular method of transforming a *Beta vulgaris* cell with a nucleotide construct, only that such nucleotide construct enters the cell. Preferred methods of the invention involve the stable integration of the nucleotide construct into the genome of the *Beta vulgaris* cell. The methods of the invention can further involve regenerating the secondary somatic embryo, or at least one transformed cell thereof, into a transformed *Beta vulgaris* plant as described supra.

Methods for transforming plants are known in the art and include, but are not limited to, Agrobacterium-mediated transformation (Townsend et al., U.S. Pat No. 5,563,055); microprojectile bombardment (see, for example, Sanford et al., U.S. Pat. No. 4,945,050); microinjection (Crossway et al. (1986) Biotechniques 4:320–334); electroporation (Riggs et al. (1986) *Proc. Natl. Acad. Sci. USA* 83:5602–5606; and direct gene transfer (Paszkowski et al. (1984) *EMBO J.* 3:2717–2722); all of which are herein incorporated by reference.

Genes of interest include, but are not limited, genes that increase disease resistance, insect resistance, nematode resistance, yield, sugar content, drought tolerance, cold tolerance, herbicide resistance and any gene that increases the economic value of the harvested portions of the *Beta vulgaris* plant. Of particular interest are genes that provide agronomically important traits. For example, insect resistance genes may encode resistance to pests such as rootworm, cutworm, European Corn Borer, and the like. Such genes include, for example, *Bacillus thuringiensis* toxic protein genes (U.S. Pat. Nos. 5,366,892; 5,747,450; 5,723,756; and 5,593,881). Herbicide resistance genes can be used to increase the resistance of a plant to a herbicide. Such herbicide resistant plants provide producers with the capability to employ improved weed management strategies. Herbicide resistance genes may include genes coding for resistance to herbicides that act to inhibit the action of acetolactate synthase (ALS), in particular the sulfonylurea-type herbicides and imidazolinones, genes coding for resistance to herbicides that act to inhibit action of glutamine synthase, such as, for example, phosphinothricin, genes coding for resistance to glyphosate and other such genes known in the art.

The methods of the invention involve exposing plant tissues to plant culture media. By "exposing" is intended placing the tissue in the vicinity of the medium wherein at least one component of the medium is able to enter the tissue. Typically, the tissue will be exposed to the medium by placing the tissue in direct contact with the medium. It is recognized, however, that the tissue can be exposed to the medium without directly contacting the medium. For example, the tissue can be exposed to a medium by placing the tissue on a filter-paper-lined surface of a plate of solid medium.

It is also recognized that the plant tissues of the invention which are exposed to a particular plant culture media may be routinely transferred to fresh plant culture media when necessary. Such routine transfers of plant tissue to fresh plant culture media are known in the art.

Plant culture media of the invention include, but are not limited to, germination media, callus induction media, embryogenesis media, initiation media, proliferation media, regeneration media and rooting media. Such media are known in the art. Any plant culture medium known in the art may be employed in the methods of the present invention. For a general descriptions plant culture media and basic techniques in plant cell, tissue and organ culture, see Evans et al eds. (1983), *Handbook of Plant Cell Culture, Vol. 1: Techniques for Propagation and Breeding* (MacMillan, London); Sharp et al. eds. (1984) *Handbook of Plant Cell Culture, Vol 2: Crop Species* (MacMillan, London); Ammirato et al. eds. (1984) *Handbook of Plant Cell Culture, Vol. 3: Crop Species* (MacMillan, London); and Evans et al. eds. (1983) *Handbook of Plant Cell Culture, Vol. 4: Techniques and Applications* (MacMillan, London); all of which are herein incorporated by reference.

The methods of the invention involve isolated plant tissues including, but not limited to, seedling tissues, callus tissues, somatic embryos, embryogenic tissue masses, secondary somatic embryos and the like. In the practice of the invention, it may be necessary to isolate desired tissues from other undesired tissues. Preferably, such isolations will be accomplished by excision with a scalpel, knife or other similar sharp-bladed instrument. Similarly, desired tissues such as embryogenic tissue masses may be subdivided into two or more pieces by excision.

The methods of the invention involve tissues of *Beta vulgaris* plants. The *Beta vulgaris* plants of the invention include, but are not limited to, the common garden beet or red beet, Swiss chard and the sugar beet (*Beta vulgaris* var. *altissima*). Preferred methods of the invention involve sugar beet plants, including, but not limited to, diploid and triploid cultivars. Any sugar beet variety known in the art may be employed in the methods of the present invention including, but not limited to, ACH199, ACH31 and ACH203.

The following examples are presented by way of illustration, not by way of limitation.

Experimental

EXAMPLE 1

Callus Initiation and Somatic Embryogenesis Using Sugar Beet Seedling Tissues

Seeds from three sugar beet lines ACH199 (triploid), ACH31 (triploid) and ACH203 (diploid) were obtained from Crystal and Maribo Beet Seed, Moorehead, Minn. USA. To remove seed covers, *Beta vulgaris* seeds were soaked in the tap water overnight and then washed under water flow. Seeds were sterilized by sequential treatment with 70% (v/v) ethanol (1 min.), 0.1% (w/v) mercuric chloride (10 min.) and 10% (v/v) household laundry bleach (20 min.) followed by four washes with sterile distilled water. Seeds were then dried on sterile filter paper. All steps were performed in a laminar flow hood.

A series of media which included additional supplements were used for callus induction, embryo proliferation and shoot formation. Phytohormones (BAP, TDZ, NAA, IAA, 2,4-D) were added to the media before autoclaving (120° C. for 20 min.). The basal medium for callus induction and embryogenesis is MS medium comprising MS basal salts, 3% sucrose, 100 mg/L myo-inositol, 0.5 mg/L nicotinic acid, 0.5 mg/L pyridoxine-HCl, 1 mg/L thiamine-HCl and 0.8% (w/v) Difco agar. The basal medium for proliferation of repetitive embryos is MSE (MS basal salts, 100 mg/L myo-inositol, 0.5 mg/L nicotinic acid, 0.5 mg/L pyridoxine-HCl, 1 mg/L thiamine-HCl).

Friable callus formation and regeneration has been described previously (Krens et al. (1989) *J. Plant Physiol* 134:651–655; Owens et al. (1992) *Plant Cell Tissue Organ Culture* 41:165–170, Jacq et al (1993) *Plant Breeding* 110:185–191). Initially, BAP was used as the primary callus-inducing agent. Later, Nielson et al. (1995) *Plant Cell Tissue Organ Culture* 41:165–170 and Roussy et al. (1996) *Plant Cell Reports* 16:142–146 reported that application of TDZ is a more effective callus-inducing agent than BAP. TDZ may exert its influence by modifying the metabolism of exogenous cytokinins (Roussy et al. (1996) *Plant Cell Reports* 16:142–146).

Figure 1B:
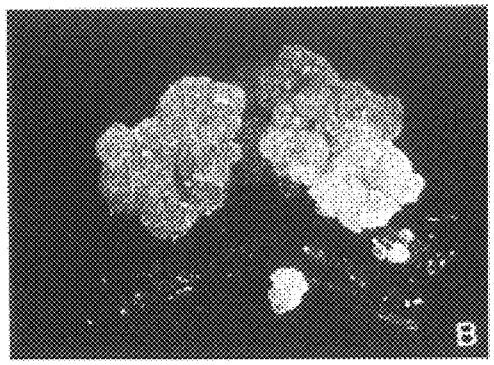

Petri dishes (100 mm×25 mm) containing 25 mL of medium were used for all experiments. Seeds were placed on MS medium, containing either BAP 2 mg/L or TDZ 1 mg/L; plates were sealed and placed in the dark place at 21° C. Cotyledons and hypocotyls (FIG. 1A) were excised from two-week-old seedlings, cut into several pieces, incised and placed on callus induction medium (MS medium supplemented with either 2 mg/L of BAP or 1 mg/l of TDZ). Plates were incubated in the dark at 21° C. Four weeks later, when explants were necrotic and dark brown, colonies of white friable callus appeared on the explant surface (FIG. 1B). Most of the callus formed on hypocotyls. Only a few colonies were found on cotyledons.

Figure 1C:
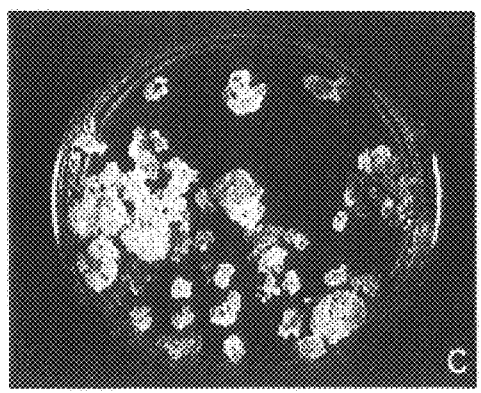

For regeneration of embryos, friable callus was transferred to callus regeneration medium (MS medium supplemented with either 1 mg/L of BAP or 1 mg/L of TDZ). The cultures were incubated at 25° C. under a photoperiod of 16 hours of light of cool, white light at an intensity of 30 $\mu$mol $m^{-2}s^{-1}$ followed by a 8 hours of darkness. Callus began to grow vigorously, and by the end of the second week, it was possible to distinguish several callus types as well as small embryos (FIG. 1C). Since every seedling was treated as a separate line, quantitative analysis can be applied to the results of the experiments.

The frequencies of callus formation and regeneration are shown in Table 1. All explants of one type from the same line (i.e. only hypocotyls) were able to produce callus, if any did. At the same time, there were only a few cases where callus formed from both cotyledons and hypocotyls of the same seedling (twice in ACH31 and four times in ACH203).

Comparing the effect of BAP and TDZ (Table 1), TDZ dramatically increased rate of callus formation from hypocotyls and plant regeneration from such callus in two out of three cultivars tested. A two-fold increase of friable callus formation from hypocotyls and nine-fold increase of plant regeneration from these calli were detected in the case of ACH31. Application of TDZ to hypocotyls of another cultivar, ACH203, provided similar results. On the other hand, no TDZ-related improvements of callus initiation were detected from cotyledons.

The methods disclosed herein using TDZ differ from the methods of Roussy et al. (1996) *Plant Cell Reports* 16:142–146) and Lenzner et al. ((1995) *Physiologia Plant* 94: 342–350). Roussy et al. (1996) *Plant Cell Reports* 16:142–146) employed leaf tissues harvested from TIBA-treated *Beta vulgaris* plants to regenerate shoots and plants from TDZ-induced callus. The methods of the present invention do not depend on the treatment of *Beta vulgaris* seedling tissues with TIBA for the regeneration of shoots and plants from TDZ-induced callus. Lenzner et al. ((1995) *Physiologia Plant.* 94:342–350) reported the production of shoots from friable callus derived from mesophyll protoplasts of a sugar beet clone referred to as "VRB," using media comprised of a combination of TDZ and an auxin, NAA. The medium used by Lenzner et al. ((1995) *Physiologia Plant.* 94:342–350) to produce the callus did not, however, contain TDZ.

Figure 1D:
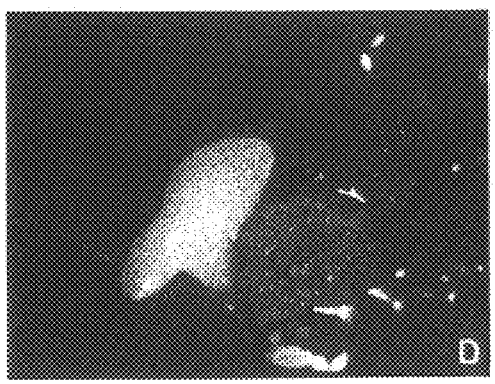

After having subcultured callus tissues on regeneration medium, friable callus grew quite fast, expanded vigorously and was almost totally necrotic after a month. At this moment a few white embryogenic structures at different stages of development became visible (FIG. 1D); however, only callus of ACH199 growing on MS+BAP at 1 mg/L produced such structures. The frequency of embryogenesis was very low. Seven separate embryos were found in two out of 40 independent callus lines.

TABLE 1

Effect of medium composition and explant type on callus induction and shoot regeneration

| Hormone | Explant type | # of lines | # of lines produced callus | %[A] | # of lines produced shoots | %[B] |
|---|---|---|---|---|---|---|
| Cultivar ACH31 | | | | | | |
| TDZ | Hypocotyls | 110 | 50 | 45 | 10 | 9 |
| | Cotyledons | 110 | 0 | 0 | 0 | 0 |
| BAP | Hypocotyls | 210 | 43 | 20 | 1 | 1 |
| | Cotyledons | 205 | 3 | 1 | 0 | 0 |
| Cultivar ACH203 | | | | | | |
| TDZ | Hypocotyls | 230 | 100 | 43 | 40 | 17 |
| | Cotyledons | 226 | 0 | 0 | 0 | 0 |

TABLE 1-continued

Effect of medium composition and explant type on callus induction and shoot regeneration

| Hormone | Explant type | # of lines | # of lines produced callus | %[A] | # of lines produced shoots | %[B] |
|---|---|---|---|---|---|---|
| BAP | Hypocotyls | 239 | 42 | 18 | 11 | 5 |
| | Cotyledons | 233 | 11 | 5 | 2 | 0.9 |
| Cultivar ACH199 | | | | | | |
| TDZ | Hypocotyls | N/A[†] | N/A | N/A | N/A | N/A |
| | Cotyledons | N/A | N/A | N/A | N/A | N/A |
| BAP | Hypocotyls | 240 | 36 | 15 | 1 | 0.5 |
| | Cotyledons | 240 | 4 | 2 | 1 | 0.5 |

[A]Number of lines producing callus/total number of lines × 100.
[B]Number of lines producing callus and regenerating/total number of lines × 100.
[†]Not available.

EXAMPLE 2

Production of Embryogenic Cultures

In vitro somatic embryogenesis can occur from different types of explants and can be induced by the auxin analogue 2,4-D in many species (Liu et al. (1996) *Plant Cell Tissue Organ Culture* 47:33–42; Sato et al. (1993) *Plant Cell Reports* 12:408–413; Finer et al. (1991) *Crit. Rev. Plant Sci.* 10:33–61). In the case of sugar beet, cytokinins are known to activate the cell cycle of many cells in the hypocotyls including cells in the vascular cambium which may develop into a calli and subepidermal cells which may develop into somatic embryos. In the examples disclosed herein, the initial somatic embryos appeared as white structures on the surface of, or embedded in, a callus mass of non-differentiated cells. It is well known that somatic embryo development is analogous to zygotic embryo development. Embryo development is characterized by a series of morphological changes leading to mature embryo. Careful examination of three-week-old callus masses revealed the presence of embryos at the different morphological stages of development including, but not limited to, the globular, heart (FIG. 1D) and torpedo stages. The most distinguishing feature of such embryos was their white coloration.

Figure 2A:
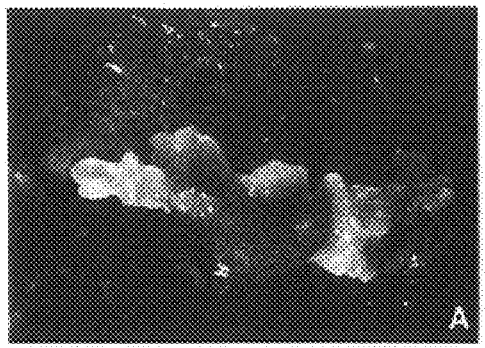
FIG. 2 is a photographic illustration of selected stages in the formation of repetitive somatic embryos. (A) White embryogenic tissue masses appear in the meristem region of a germinated embryo. (B) Embryogenic tissue masses isolated from a germinated embryo turn dark in liquid culture with the appearance of white embryogenic outgrowths. (C) Development of an embryo into a plant. (D) Sugar beet plant produced from a secondary somatic embryo. The embryo gave rise to a normal shoot.
Figure 2B:
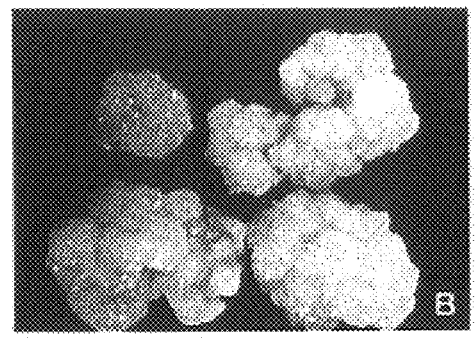

The embryos germinated quickly when transferred to fresh medium either supplemented with phytohormones or not. Embryos transferred to MS medium containing BAP or TDZ not only formed multiple shoots but also retained white embryogenic tissues appearing as inclusions in the meristem (FIG. 2A). These embedded tissues were manually isolated, separated and transferred into liquid medium (MS medium+ BAP 0.2 mg/L). The cultures were maintained at constant agitation (100 rpm) in the dark with biweekly changes of the medium. The white embryogenic tissue masses expanded in two weeks and snow-white fresh outgrowths formed on the surface of older tissues (FIG. 2B). Clumps of white embryogenic tissue masses were divided and transferred to fresh medium for further proliferation. A couple of such passages was enough to generate a large number of white clumps. Part of these tissues was used for the optimization of culture medium.

The present invention provides a method to select and maintain repetitive embryonic cultures without losing regeneration and root formation capabilities, despite fast and uncontrollable conversion of embryos to normal plants. It was impossible to stop regeneration of the primary somatic embryos. Once such embryos were transferred to fresh medium, they turned to normal plants. Fortunately, the inclusions of embryogenic tissues detected by snow-white color were found embedded in swollen meristems after the close evaluation of the germinating embryos. To liberate these proembryonic tissues and to stimulate the formation of more embryos, the explants were excised manually and dispersed in a liquid medium to form a suspension culture. An enriched medium (MSE, sucrose 6%, BAP 0.1 mg/L and glycine 2 mg/L) containing a high level of sucrose was used for this purpose to prevent precocious germination and to enable deposition of storage reserves. Although it was possible to obtain a pure embryogenic culture in the first round of subcultivation (FIG. 1D), all subsequent passages produced a mixture of vitrified meristematic tissues and embryos.

EXAMPLE 3

Optimization of Proliferation Medium

The optimization of proliferation medium was conducted through several stages. Each stage lasted for two weeks. The most appropriate combination of media components was used to prepare media for the next round of optimization (Table 2). The medium consisting of MSE, sucrose 6%, BAP 0.1 mg/L and glycine 2 mg/L was found the most appropriate for maintaining the proliferation of embryogenic tissue masses in culture. Further attempts to optimize the proliferation medium by modification of sucrose content did not lead to any further improvement.

Several effects of phytohormones on embryogenic tissues were found during medium optimization. First of all, presence of 2,4-D in the medium had a negative effect on embryo proliferation, opposite to what was found with other species. TDZ, on the other hand, induced the regeneration of embryos as was indicated by vigorous growth and red coloration as well as by the absence of embryogenic tissue masses in culture.

In general, TDZ caused very quick proliferation of tissue and intensified production of anthocyanins, as was indicated by the red color of the cultures. At the same time TDZ did not cause necrosis. Even after TDZ was removed from the medium and the cultures went through several passages with other phytohormones, the tissues continued to grow extremely fast and retained their red color. Glutamine and 2,4-D caused bleaching of vitrified tissues, whereas cultures growing in other media usually exhibited red color of varying intensity. In all cases, however, white embryogenic tissues masses retained their white color and compact arrangement and were in contrast to the meristematic tissues of red color and looser texture.

TABLE 2

Effect of media on repetitive embryogenic culture

I. MSE, BAP 0.2 mg/L, glutamine 2 mg/L, pH 5.7, and carbon source:

| | |
|---|---|
| Sucrose 6% | A lot of repetitive white embryos |
| Sorbitol 6% | No growth, total necrosis |
| Mannitol 6% | No growth, total necrosis |

II. MSE, sucrose 6% glutamine 2 mg/L, pH 5.7, and phytohormones:

| | |
|---|---|
| BAP 0.1 mg/L | Most tissues are red or dark yellow, 10% are white embryos |
| Zea 0.1 mg/L | Slowly growing, mostly meristematic, vitrified tissues |
| Kin 0.1 mg/L | Slowly growing, mostly meristematic, vitrified tissues |
| BAP 0.1, NAA 0.1 mg/L | Most tissues are red or dark yellow; 25% are white embryos |
| BAP 0.1, TDZ 1 mg/L | Vigorously expanded dark red tissues, no white embryos |

III. MSE, sucrose 6% BAP 0.1 mg/l, pH 5.7 and amino acids:

| | |
|---|---|
| Glycine 2 mg/L | Tissues are light yellow; 30% are white embryos |
| Glycine 200 mg/L | Slowly growing, mostly meristematic, vitrified tissues |
| Glutamine 2 mg/L | Slowly growing, dark yellow tissues |
| Glutamine 200 mg/L | Slowly growing, dark yellow tissues |
| Glycine 2 mg/L and Glutamine 2 mg/L | Tissues are light yellow; 30% are white embryos |

IV. MSE, sucrose 6% glycine 2 mg/L, pH 5.7, and phytohormones:

| | |
|---|---|
| BAP 1 mg/L | Vigorously growing, vitrified tissues with 10% white embryos |
| BAP 0.1 mg/L | Light yellow tissues with 25% of white clumps |
| BAP 0.05 mg/L | Light yellow tissues with 25% of white clumps |
| BAP 0.01 mg/L | Necrotic tissue with some white embryos; growth is stunted |
| TDZ 1 mg/L | Vigorously expanded dark red culture, no white embryos |
| TDZ 0.1 mg/L | Vigorously expanded dark red culture with 20% white embryos |
| TDZ 0.05 mg/L | Vigorously expanded dark red culture with 20% white embryos |
| 2,4D 0.1 mg/L | Pale yellow tissues with white embryos; red pigmentation is repressed |
| BAP 0.1 & TDZ 0.1 mg/L | Vigorously expanded dark red culture with 20% white clumps |
| BAP 0.05 & TDZ 0.01 | Light yellow tissues with 25% white clumps |
| BAP 0.1 & 2,4D 0.1 mg/L | Pale yellow tissues with white embryos; red pigmentation is repressed |
| BAP 0.1 & 2,4D 0.01 mg/L | Light yellow tissues with 25% white clumps |

V. MSE, BAP 0.1 mg/L, glycine 2 mg/L, pH 5.7, and sucrose at:

| | |
|---|---|
| 3% | Necrosis of all tissues |
| 6% | A lot of repetitive white embryos |
| 8% | Growth is inhibited |
| 10% | Growth is inhibited |
| 12% | Growth is inhibited |

TABLE 2-continued

Effect of media on repetitive embryogenic culture

VI. MSE, sucrose 6%, glycine 2 mg/L, BAP 0.1 mg/L, and pH:

| | |
|---|---|
| 4.0 | Light yellow tissues with 25% white clumps |
| 5.0 | Light yellow tissues with 25% white clumps |
| 6.0 | Light yellow tissues with 25% white clumps |
| 7.0 | Light yellow tissues with 25% white clumps |

(Italic font indicates the best medium selected at a specific round)

EXAMPLE 4

Regeneration of Sugar Beet Plants

Figure 2C:
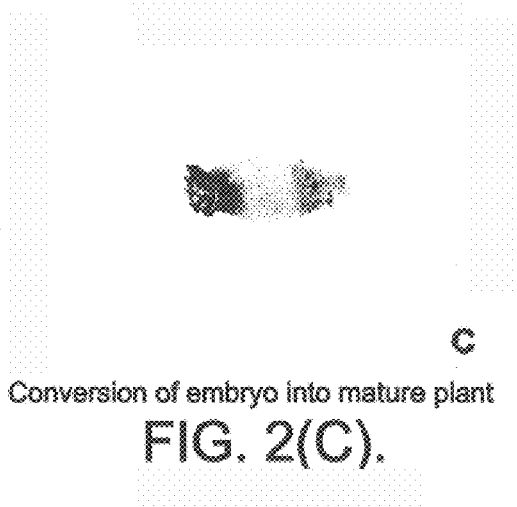
Figure 2D:
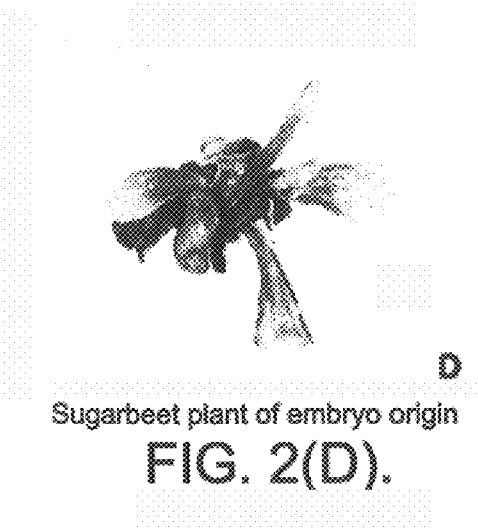

Somatic embryos produced as described in Example 3 started to germinate as soon as they were transferred to a medium comprising MS basal salts, 3% sucrose and either BAP or TDZ under light. Regeneration began with green or red coloration of an embryo accompanied by formation of primary leaves and roots (FIG. 2C). Since the regeneration medium contained cytokinins, the primary roots were reduced while the shoots developed (FIG. 2D).

Figure 3:
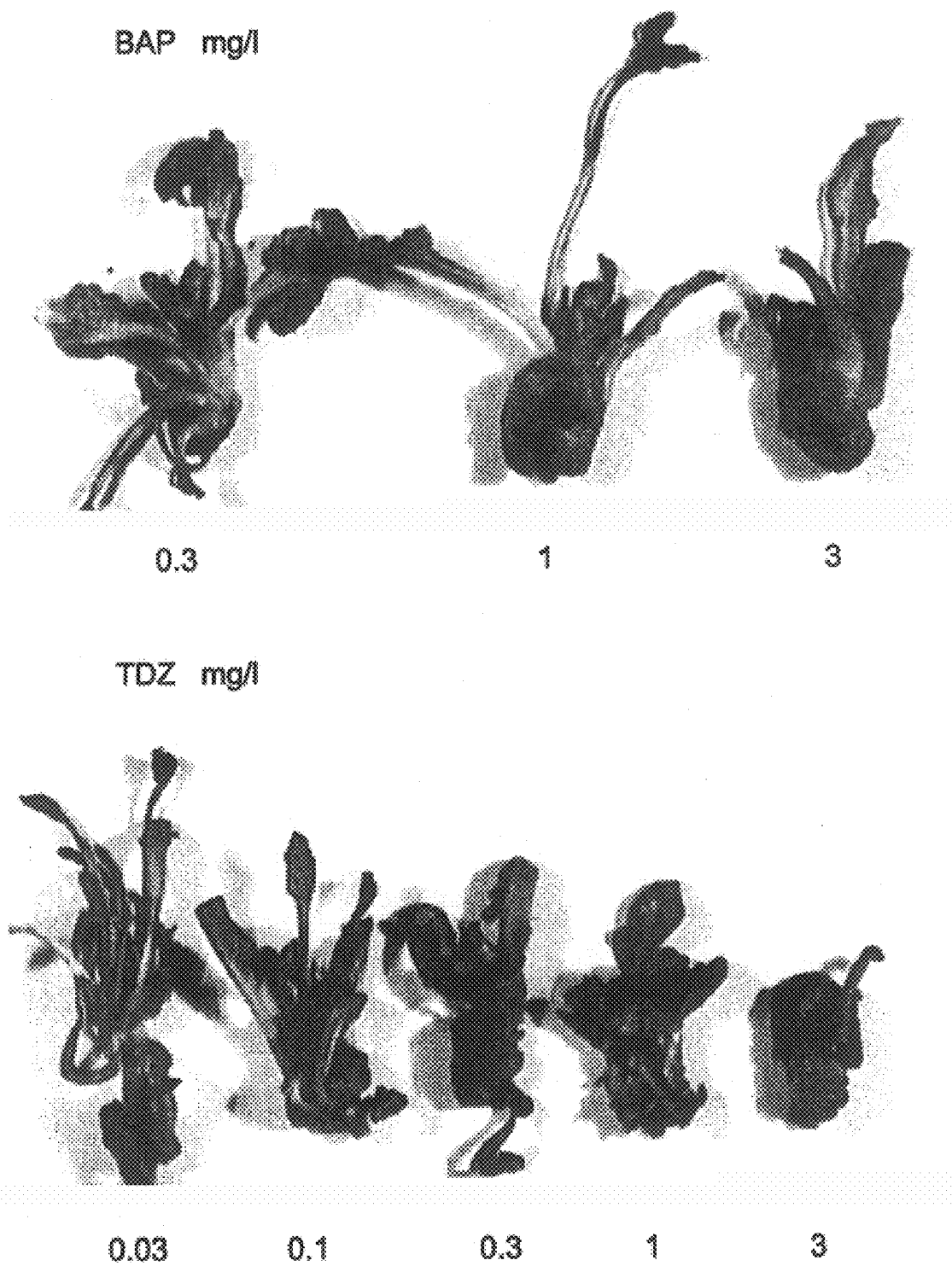
FIG. 3 is a photographic illustration of the phenotypic effect of different phytohormones on plant regeneration three weeks after placing secondary somatic embryos on regeneration media comprising either BAP (top panel) or TDZ (bottom panel) at the concentrations indicated in the figure.

To select the best medium for embryo germination, a series of concentrations of BAP and TDZ was tested. The phenotypic effect of applied phytohormones was estimated after three weeks (FIG. 3). TDZ at 0.03 mg/L was the most effective for adventitious shoot formation among the other concentrations tested, 0.03, 0.1, 0.3, 1 and 3 mg/l (FIG. 3). Higher concentrations of TDZ caused vitrification of tissues.

TDZ was found to be a preferred phytohormone for regeneration of sugar beet plants. Even low concentrations did not cause vitrification of tissues while producing more adventitious shoots.

The invention provides efficient methods for regenerating sugar beet plants. The regeneration of sugar beet plants using the methods disclosed herein takes less than six months as shown in Table 3.

TABLE 3

Sugar beet somatic embryo culture: timeframe

| Step: | Weeks |
|---|---|
| 1. SEED GERMINATION | 3 |
| 2. CALLUS INITIATION | 6 |
| 3. EMBRYO INITIATION | 3 |
| 4. REPETITIVE EMBRYOS INITIATION | 2 |
| 5. REPETITIVE EMBRYO PROLIFERATION | 2 and more* |
| 6. REGNERATION | 3 |
| 7. ROOTING | 4 |
| Total: | 23 |

*Can be run over long periods of time provided that subcultivations are performed on the biweekly basis All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for producing secondary somatic embryos of *Beta vulgaris* comprising:
   (a) exposing at least one somatic embryo to initiation medium;
   (b) isolating at least one embryogenic tissue mass that develops on said somatic embryo;
   (c) exposing said isolated embryogenic tissue mass to proliferation medium;
   (d) isolating an embryogenic outgrowth from said embryogenic tissue mass; and
   (e) exposing said isolated embryogenic outgrowth to regeneration medium to form a secondary somatic embryo.

2. The method of claim 1 wherein said initiation medium comprises at least one cytokinin.

3. The method of claim 2 wherein said cytokinin is selected from the group consisting of BAP, TDZ, kinetin and zeatin.

4. The method of claim 1 wherein said initiation medium is auxin-free.

5. The method of claim 1 wherein said embryogenic tissue mass develops from a shoot apex of said somatic embryo during germination of said somatic embryo.

6. The method of claim 5 wherein said embryogenic tissue mass is embedded in said shoot apex.

7. The method of claim 1 wherein at least one secondary somatic embryo forms on said isolated embryogenic outgrowth.

8. The method of claim 1 further comprising a multiplying step, said step comprising transferring said isolated embryogenic outgrowth or part thereof to a fresh medium, wherein said fresh medium is proliferation medium.

9. The method of claim 8 wherein said multiplying step is repeated at least one additional time.

10. The method of claim 1 wherein said proliferation medium comprises at least one cytokinin.

11. The method of claim 10 wherein said proliferation medium comprises at least one cytokinin selected from the group consisting of BAP, TDZ, kinetin and zeatin.

12. The method claim 10 wherein said proliferation medium further comprises sucrose at a concentration that is greater than 3% (w/v).

13. The method of claim 10 wherein said proliferation medium further comprises glycine.

14. The method of claim 1 wherein said somatic embryo is produced by a method comprising:
   (a) producing callus from *Beta vulgaris* seedling tissue; and
   (b) inducing said callus to form at least one somatic embryo.

15. The method of claim 14 wherein said seedling tissue is a hypocotyl or a cotyledon.

16. The method of claim 15 wherein said callus is friable callus.

17. The method of claim 16 wherein said friable callus is produced by exposing said seedling tissue to callus induction medium.

18. The method of claim 17 wherein said friable callus is induced to form said somatic embryo by exposing said friable callus to embryogenesis medium.

19. The method of claim 18 wherein at least one, of said callus induction medium and said embryogenesis medium, comprises at least one cytokinin.

20. The method of claim 19 wherein at least one, of said callus induction medium and said embryogenesis medium, comprises at least one cytokinin selected from the group consisting of BAP, TDZ, kinetin and zeatin.

21. The method of claim 1 wherein satid *Beta vulgaris* is a sugar beet plant.

22. The method of claim 1 wherein said regeneration medium comprises a cytokinin.

23. The method of claim 22 wherein said regeneration medium comprises a cytokinin selected from the group consisting of BAP, TDZ, kinetin and zeatin.

24. The method of claim 1 further comprising regenerating said secondary somatic embryo into a plant.

25. The method of claim 24 wherein said regenerating further comprises inducing root formation.

26. The method of claim 25 wherein said inducing root formation comprises exposing said secondary somatic embryo, or shoot thereof, to a medium comprising an auxin.

27. A method for producing a *Beta vulgaris* plant comprising:
   (a) exposing at least one somatic embryo to initiation medium;
   (b) isolating at least one embryogenic tissue mass that develops on said somatic embryo;
   (c) exposing said isolated embryogenic tissue mass to proliferation medium;
   (d) isolating an embryogenic outgrowth from said embryogenic tissue
   (e) exposing said isolated embryogenic outgrowth to regeneration medium to form a secondary somatic embryo, and
   (f) regenerating said secondary somatic embryo into a plant.

28. The method of claim 27 further comprising a multiplying step, said step comprising transferring said isolated embryogenic outgrowth or part thereof to a fresh medium, wherein said fresh medium is proliferation medium.

29. The method of claim 28 wherein said multiplying step is repeated at least one additional time.

30. The method of claim 27 further comprising inducing root formation.

* * * * *

UNITED STATES PATENT AND TRADEMARK OFFICE
CERTIFICATE OF CORRECTION

PATENT NO.   : 6,555,375 B1
DATED        : April 29, 2003
INVENTOR(S)  : Golovko It is certified that error appears in the above-identified patent and that said Letters Patent is hereby corrected as shown below:

<u>Column 20,</u>
Line 11, after "tissue" insert -- mass; --.

Signed and Sealed this

Second Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,555,375 B1
DATED          : April 29, 2003
INVENTOR(S)    : Golovko It is certified that error appears in the above-identified patent and that said Letters Patent is hereby corrected as shown below:

Title page,
Item [*] Notice, delete the phrase "by 308" and insert -- by 0 days --

Signed and Sealed this

Eighth Day of March, 2005

JON W. DUDAS
*Director of the United States Patent and Trademark Office*